United States Patent
Maciejewski et al.

(10) Patent No.: US 10,259,830 B2
(45) Date of Patent: Apr. 16, 2019

(54) [BIS(TRIHYDROCARBYLSILYL)AMINOSILYL]-FUNCTIONALIZED STYRENE AND A METHOD FOR ITS PREPARATION

(71) Applicants: SYNTHOS S.A., Oswiecim (PL); FUNDACJA UNIWERSYTETU IM. ADAMA MICKIEWICZA W POZNANIU, Poznan (PL)

(72) Inventors: Hieronim Maciejewski, Poznan (PL); Ireneusz Kownacki, Poznan (PL); Bogdan Marciniec, Swarzedz (PL)

(73) Assignees: SYNTHOS S.A., Oswiecim (PL); FUNDACJA UNIWERSYTETU IM. ADAMA MICKIEWICZA W POZNANIU, Poznan (PL)

( * ) Notice: Subject to any disclaimer, the term of this patent is extended or adjusted under 35 U.S.C. 154(b) by 0 days.

(21) Appl. No.: 15/565,338

(22) PCT Filed: Apr. 8, 2016

(86) PCT No.: PCT/EP2016/057735
§ 371 (c)(1),
(2) Date: Oct. 9, 2017

(87) PCT Pub. No.: WO2016/162473
PCT Pub. Date: Oct. 13, 2016

(65) Prior Publication Data
US 2018/0065996 A1 Mar. 8, 2018

(30) Foreign Application Priority Data
Apr. 10, 2015 (EP) ..................... 15461526

(51) Int. Cl.
C07F 7/10 (2006.01)
C08F 12/26 (2006.01)
C08F 212/14 (2006.01)
C08F 230/08 (2006.01)
C08F 236/10 (2006.01)
C07C 15/46 (2006.01)

(52) U.S. Cl.
CPC ............... *C07F 7/10* (2013.01); *C08F 12/26* (2013.01); *C08F 212/14* (2013.01); *C08F 230/08* (2013.01); *C08F 236/10* (2013.01); *C07C 15/46* (2013.01)

(58) Field of Classification Search
None
See application file for complete search history.

(56) References Cited

U.S. PATENT DOCUMENTS

| | | | |
|---|---|---|---|
| 3,109,871 A | 11/1963 | Zelinski et al. | |
| 3,253,008 A | 5/1966 | Fink | |
| 4,196,154 A | 4/1980 | Tung et al. | |
| 4,835,216 A | 5/1989 | Morikawa et al. | |
| 4,861,742 A | 8/1989 | Bronstert et al. | |
| 4,894,409 A | 1/1990 | Shimada et al. | |
| 4,935,471 A | 6/1990 | Halasa et al. | |
| 5,550,203 A | 8/1996 | Engel et al. | |
| 6,515,087 B2 | 2/2003 | Hsu et al. | |
| 6,627,721 B1 | 9/2003 | Rodewald et al. | |
| 6,627,722 B2 | 9/2003 | Rodewald et al. | |
| 6,630,552 B1 | 10/2003 | Rodewald et al. | |
| 6,670,471 B1 | 12/2003 | Rodewald et al. | |
| 9,120,890 B2 * | 9/2015 | Ishino ................... | B60C 1/0016 |
| 2004/0044157 A1 | 3/2004 | Halasa et al. | |
| 2004/0044202 A1 | 3/2004 | Halasa et al. | |
| 2004/0063884 A1 | 4/2004 | Halasa et al. | |
| 2004/0122194 A1 | 6/2004 | Halasa et al. | |
| 2004/0122224 A1 | 6/2004 | Halasa et al. | |
| 2005/0131181 A1 | 6/2005 | Halasa et al. | |
| 2007/0123631 A1 | 5/2007 | Halasa et al. | |
| 2009/0023861 A1 | 1/2009 | Shimakage et al. | |
| 2010/0116404 A1 | 5/2010 | Lechtenboehmer et al. | |
| 2011/0275756 A1 | 11/2011 | Ito et al. | |
| 2012/0041134 A1 | 2/2012 | Ito et al. | |
| 2014/0275430 A1 | 9/2014 | Ishino et al. | |
| 2018/0072101 A1 | 3/2018 | Janowski et al. | |
| 2018/0072821 A1 | 3/2018 | Janowski et al. | |

FOREIGN PATENT DOCUMENTS

| | | |
|---|---|---|
| EP | 0 316 255 | 5/1989 |
| EP | 0590491 | 4/1994 |
| EP | 1 792 892 | 6/2007 |
| EP | 2 182 028 | 5/2010 |
| EP | 2 196 326 | 6/2010 |
| EP | 2277940 | 1/2011 |
| EP | 2749575 | 7/2014 |
| EP | 2 772 515 | 9/2014 |
| JP | 2004-059781 | 2/2004 |

(Continued)

OTHER PUBLICATIONS

International Search Report for PCT/EP2016/057757, dated Jun. 16, 2016, 2 pages.
International Search Report for PCT/EP2016/057834, dated Jun. 16, 2016, 4 pages.
Abstract of Rasul et al., "Hydrosilylation reactions of tetramethyldisilazanes and their derivatives" *Journal of Organometallic Chemistry*, vol. 655, iss. 1-2: 115-119 (Aug. 2002).
Abstract of Rietz et al., "Reaktionen von Bis(trimethylsilyl)amino-substituierten Chlorsilanen [(Me3Si)2N]Me2—nPhnSiCl (n=0, 1, 2) mit Lithium—Darstellung von Bis(trimethylsilyl)amino-substituierten Silyllithiumverbindungen and Disilanen" *Journal of Organometallic Chemistry*, vol. 556, Issues 1-2, Apr. 15, 1998, pp. 67-74.

(Continued)

*Primary Examiner* — Clinton A Brooks
*Assistant Examiner* — Kofi Adzamli
(74) *Attorney, Agent, or Firm* — Nixon & Vanderhye P.C.

(57) ABSTRACT

The invention relates to [bis(trihydrocarbylsilyl)aminosilyl]-functionalized styrene and a method for its preparation. The invention further relates to the use of the styrene derivative in the preparation of a copolymer thereof.

24 Claims, No Drawings

(56) References Cited

FOREIGN PATENT DOCUMENTS

| | | |
|---|---|---|
| WO | WO 2011/076377 | 6/2011 |
| WO | WO 2016/162482 | 10/2016 |
| WO | WO 2016/162528 | 10/2016 |
| WO | WO 2018/065486 | 4/2018 |
| WO | WO 2018/065494 | 4/2018 |

OTHER PUBLICATIONS

International Preliminary Report on Patentability issued in PCT/EP2016/057757 dated Oct. 10, 2017.
International Preliminary Report on Patentability issued in PCT/EP2016/057834 dated Oct. 10, 2017.
International Search Report issued in PCT/EP2017/075251 dated Jan. 18, 2018.
International Search Report issued in PCT/EP2017/075262 dated Jan. 18, 2018.
Written Opinion of the International Searching Authority issued in PCT/EP2017/075251 dated Jan. 18, 2018.
Written Opinion of the International Searching Authority issued in PCT/EP2017/075262 dated Jan. 18, 2018.
International Search Report for PCT/EP2016/057735 dated Jun. 17, 2016, 4 pages.
Lee, S. et al., "Palladium-catalyzed synthesis of arylamines from aryl halides and lithium bis(trimethylsilyl) amide as an ammonia equivalent", Org. Lett., 2001 3(17), pp. 2729-2732.
Zapilko, C. et al., "Advanced Surface Functionalization of periodic mesoporous Silica: Kinetic Control by Trisilazane reagents", J. Am. Chem. Soc., 2006, 128(50), pp. 16266-16276.

* cited by examiner

[BIS(TRIHYDROCARBYLSILYL) AMINOSILYL]-FUNCTIONALIZED STYRENE AND A METHOD FOR ITS PREPARATION

This application is the U.S. national phase of International Application No. PCT/EP2016/057735 filed Apr. 8, 2016 which designated the U.S. and claims priority to EP Patent Application No. 15461526.4 filed Apr. 10, 2015, the entire contents of each of which are hereby incorporated herein by reference.

FIELD OF THE INVENTION

The invention relates to [bis(trihydrocarbylsilyl)aminosilyl]-functionalized styrene and a method for its preparation. The styrene derivative can be particularly applied in the production of styrene-butadiene rubbers having unique physicochemical properties. These rubbers are used in the preparation of compounded rubbers, for the manufacture of car tires.

BACKGROUND OF THE INVENTION

An important parameter that determines whether styrene-butadiene rubber can be used in the manufacture of tires and other elastomeric commercial products is the rubber's compatibility with commonly used fillers, such as carbon black and silica. An increase in the interactions between styrene-butadiene rubber and inorganic filler can be achieved by introducing appropriate functional group-containing polymeric fragments that enhance the polymer's affinity to the applied filler.

U.S. Pat. No. 4,935,471 B discloses that the introduction of nitrogen-containing functional groups into the polymer structure results in a strong enhancement of the affinity of functionalized polymers to carbon black. A clear increase in the compatibility of modified polybutadiene with the filler was observed even after the introduction of one terminal functional group containing a tertiary nitrogen atom (e.g. —CN or —NMe$_2$) into polymer chains. In addition to the increase in affinity of the modified polymer to the filler, a clear improvement in filler dispersion in the rubber compound was observed. In the examples of U.S. Pat. No. 4,935,471, methods for the synthesis of initiators of living anionic polymerization based on aromatic N-heterocyclic compounds such as pyrrole, imidazole, pyrazole, pyrazine, pyrimidine, pyridazine, and phenanthroline derivatives and their use in the production of N-functionalized polybutadienes are described. A similar approach is disclosed in U.S. Pat. No. 6,515,087 B, EP 0 590 491 A1 and WO2011/076377 A, where acyclic and cyclic amines are employed for the preparation of active initiators for anionic polymerization. In a further step, amines are used for the preparation of di-N-functionalized styrene-butadiene polymers.

Silicon and/or nitrogen atom-containing vinyl compounds are further taught in US 2004/0044202 A1, EP 2 749 575 A1, US 2012/0041134 A1, EP 2 277 940 A1, and US 2004/0063884 A1.

The synthesis of di-N-functionalized styrene-butadiene polymers is also disclosed in U.S. Pat. Nos. 4,196,154 B, 4,861,742 B and 3,109,871 B. However, to obtain the above polymers, amino-functional aryl methyl ketones are applied as reagents. The latter plays also the role of a functionalizing agent and polymerization terminating agent. The above N-modification methods only allow the preparation of polydienes containing no more than two amino-functional groups per polymer chain.

Another approach to prepare N-functionalized polymers with different N-functional group contents consists in the introduction of suitable styrene monomers into the polymer chain. The controlled introduction of the styrene monomers to the reaction system will result in a wide range of styrene-butadiene rubbers with different N-functional group contents, thereby with different dispersion properties for inorganic fillers. US2007/0123631 A1 discloses the preparation of N-functionalized styrene monomers via the reaction of a diverse range of acyclic and cyclic lithium amides (LiNR$^1$R$^2$, e.g. LiNEt$_2$, LiNMePh, LiN(SiMe$_3$)$_2$, LiNC$_4$H$_8$, and LiNC$_5$H$_{10}$) with 1,3- or 1,4-divinylobenzene, 1,3-di (isopropylene)benzene or a mixture of isomeric chloromethylstyrenes that in a further step are used in the preparation of styrene-butadiene rubbers with different contents of amino-functional groups.

EP 2 772 515 A1 teaches a conjugated diene polymer obtained by polymerizing a monomer component including a conjugated diene component and a silicon-containing vinyl compound. The silicon-containing vinyl compound may be a silyl-substituted styrene. However, the compounds according to EP 2 772 515 A1 are hydrolytically unstable under the typical processing conditions, compare the N,N-bis(SiMe$_3$)$_2$ aniline derivatives disclosed in Organic Letters 2001, 3, 2729.

The prior art is only concerned with the preparation of N-functionalized polydienes with a different content of N-functionality which can interact with commonly-used fillers, i.e. silica and carbon black through non-covalent interactions. However, standard formulations very often comprise both types of filler, silica and carbon black, in different ratios.

Therefore, it was the object of the present invention to overcome the disadvantages associated with the prior art and to provide functionalized styrene derivatives whose application in the synthesis of polydienes leads to in-chain modified SBR polymer compositions that have better affinity to both of the two typical fillers commonly applied in tire production, i.e. silica and carbon black. The functionalized styrene derivatives should also be hydrolytically more stable than those of EP 2 772 515 A1.

SUMMARY OF THE INVENTION

It has now surprisingly been found that this object is solved by the [bis(trihydrocarbylsilyl)aminosilyl]-functionalized styrene derivatives of formula I

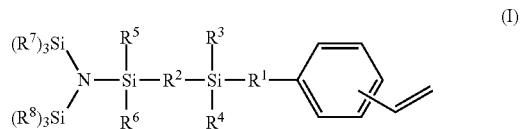

wherein R$^1$ and R$^2$ can be the same or different and represent a member selected from the group consisting of:
a) a single bond;
b) —(CH$_2$)$_n$—, wherein n represents an integer from 1 to 12;
c) —(CH$_2$CH$_2$Y)$_n$—, wherein n represents an integer from 1 to 12, and Y can independently be oxygen or sulfur;
d) —CH$_2$—(CH$_2$CH$_2$Y)$_n$—CH$_2$—, wherein n represents an integer from 1 to 12, and Y can independently be oxygen or sulfur;

e) —(CH$_2$CH$_2$NR)$_n$—, wherein n represents an integer from 1 to 12, and R can independently represent an alkyl group containing from 1 to 10 carbon atoms, or an aryl or aralkyl group containing from 6 to 10 carbon atoms;

f) —CH$_2$—(CH$_2$CH$_2$NR)$_n$—CH$_2$—, wherein n represents an integer from 1 to 12, and R can independently represent an alkyl group containing from 1 to 10 carbon atoms, or an aryl or aralkyl group containing from 6 to 10 carbon atoms;

g) —(CH$_2$SiR$_2$)$_n$—, wherein n represents an integer from 1 to 12, and R can independently represent an alkyl group containing from 1 to 10 carbon atoms, or an aryl or aralkyl group containing from 6 to 10 carbon atoms;

h) —CH$_2$—(CH$_2$SiR$_2$)$_n$—CH$_2$—, wherein n represents an integer from 1 to 12, and R can independently represent an alkyl group containing from 1 to 10 carbon atoms, or an aryl or aralkyl group containing from 6 to 10 carbon atoms;

i) —(OSiR$_2$)$_n$—, wherein n represents an integer from 1 to 12, and R can independently represent an alkyl group containing from 1 to 10 carbon atoms, or an aryl or aralkyl group containing from 6 to 10 carbon atoms; and j) —CH$_2$—(OSiR$_2$)$_n$—CH$_2$—, wherein n represents an integer from 1 to 12, and R can independently represent an alkyl group containing from 1 to 10 carbon atoms, or an aryl or aralkyl group containing from 6 to 10 carbon atoms;

wherein $R^3$, $R^4$, $R^5$, and $R^6$ can be the same or different and represent an alkyl group containing from 1 to 10 carbon atoms, or an aryl or aralkyl group containing from 6 to 10 carbon atoms; and $R^7$ and $R^8$ can be the same or different, and each $R^7$ and $R^8$ independently represents an alkyl group containing from 1 to 10 carbon atoms, or an aryl or aralkyl group containing from 6 to 10 carbon atoms.

The compounds of formula (I) are monomeric styrene derivatives. Employing these styrene derivatives (containing the moiety $\{(R^8)_3Si\}\{(R^7)_3Si\}NSiR^6R^5$—$(R^2)$—$SiR^3R^4$—$(R^1)$— in their structure) in the synthesis of SBR polymers not only increases the affinity of the modified polymers to the commonly used fillers via non-covalent interactions, but also provides for covalent interactions between the modified polymer and filler, in particular silica, due to the reactivity of the $\{(R^8)_3Si\}\{(R^7)_3Si\}NSiR^6R^5$— moiety.

Surprisingly, it was found that the preparation of rubber compounds based on styrene-butadiene rubbers modified with a small amount of styrene comonomer (I) leads to copolymers that give rubber compositions having by 32% better wet grip and by 24% better rolling resistance as compared to those prepared on the basis of non-functionalized styrene derivatives.

Further, it was found that the bis(trimethylsilyl)amine- or bis(trimethylsilyl)aminealkyl-substitued styrene derivatives disclosed in EP 2 772 515 A1 have a serious drawback, insofar as they are hydrolytically unstable, due to the high reactivity of the (Me$_3$Si)$_2$N—R— group with water, particularly under acidic or basic conditions (compare Organic Letters 2001, 3, 2729). Thus, the hydrolysis of molecular or macromolecular compounds containing e.g. the moiety (Me$_3$Si)$_2$N—R— leads to the formation of Me$_3$SiOSiMe$_3$, with simultaneous restoration of free H$_2$N—R— groups which in the final rubber composition can interact with the carbon black only by non-covalent bonds and with the silica by hydrogen bonding.

In contrast to those styrene derivatives containing a bis(trialkylsilyl)amine moiety ((R$_3$Si)$_2$N—R—), see e.g. EP 2 772 515 A1, compounds according to the present invention have a nitrogen atom that is surrounded by three silyl groups, such as in $\{(R^8)_3Si\}\{(R^7)_3Si\}NSiR^6R^5$—$R^2$—. The styrene derivatives of the present invention are surprisingly hydrolytically more stable (compare Organometallic Chemistry 2002, 655, 115, teaching (RMe$_2$Si)$_2$NSiMe$_3$ derivatives which were isolated by extraction of the organic layer with an aqueous solution of NH$_4$Cl).

Further, and in contrast to simple [(R$_3$Si)$_2$N—R-]-functionalized polymers, any partial hydrolysis of groups of the type $\{(R^8)_3Si\}\{(R^7)_3Si\}NSiR^6R^5$—$R^2$— in the copolymer as functionalized according to the present invention will at elevated temperature advantageously lead to the formation of reactive silanol groups (HOSiR$^6$R$^5$—R$^2$—). These groups are capable of the formation of a stable covalent bond with the silica filler through a [(SiO$_2$)O$_3$Si]—O—SiMe$_2$-R— bond sequence by the cross-condensation reaction between hydroxyl groups on silica surface [(SiO$_2$)O$_3$Si]—OH and HOSiMe$_2$-R-functionalized polymer as it was disclosed in J. Am. Chem. Soc. 2006, 128, 16266 for molecular trisilylamine derivatives of the type (RMe$_2$Si)$_2$NSiMe$_2$R', used in the modification of MCM-41's surface. Moreover, the remaining (Me$_3$Si)$_2$N—SiMe$_2$- moieties are capable to interact with carbon filler (e.g. carbon black) via a non-covalent interaction.

According to a third aspect, the invention relates to the use of the styrene derivative of structural formula (I) as defined above, in the production of an elastomeric copolymer.

Details of the Invention

In a first aspect, the invention relates to the styrene derivative of Formula I. In a second aspect, the invention relates to a method for the preparation of the styrene derivative of formula (I). In a third aspect, the invention related to the use of the styrene derivative of formula (I) in the preparation of a copolymer thereof.

The Styrene Derivative of Formula (I)

In a preferred embodiment of the first aspect, the styrene derivative is a para or meta isomer, i.e. is of formula (Ia) or (Ib)

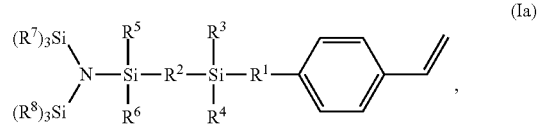

(Ia)

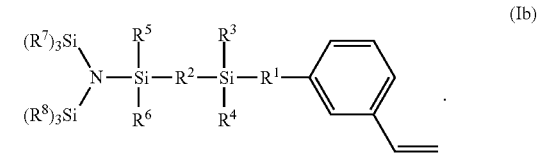

(Ib)

It is further preferred that the styrene derivative has $R^1$ selected from the group consisting of:

a) a single bond; and b) —(CH$_2$)$_n$—, wherein n represents an integer from 1 to 12.

More preferably, $R^1$ is b) —(CH$_2$)$_n$—, wherein n represents an integer from 1 to 5, preferably n represents an integer from 1 to 3, in particular n is 1.

Furthermore, it is preferred that $R^2$ is b) —$(CH_2)_n$—, wherein n represents an integer from 1 to 12, preferably n represents an integer from 1 to 5, more preferably n represents an integer from 1 to 3, in particular n is 2.

Also preferred are compounds of the general formula (I) having $R^2$=—$CH_2$—$CH_2$—, i.e. n (of $R^2$)=2; wherein $R^3$, $R^4$, $R^5$, $R^6$, $R^7$, and $R^8$ are the same or different and represent -Me or -Ph groups; and $R^1$ represents a single bond, or a —$(CH_2)_n$— group wherein n (of $R^1$) assumes values of 1 or 2, preferably 1.

It is generally preferred that $R^2$ in the styrene derivative of formula (I) is $(CH_2)_2$. Preferred styrene derivatives of this type are selected from any one of formulae (1), (2), (3), (4), (5), and (6)

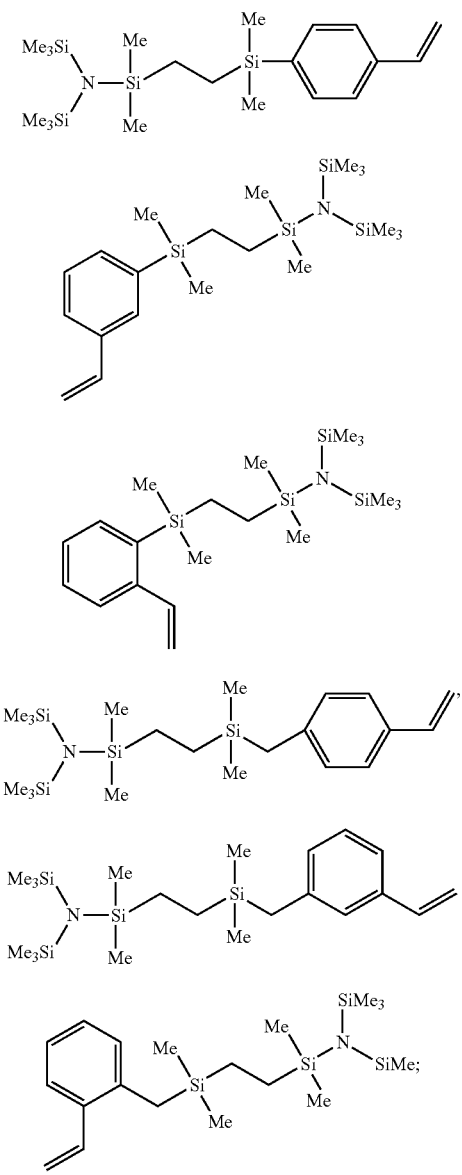

more preferably the styrene derivative of formula (I) is selected from any one of formulae (1), (2), (4), and (5); most preferably the styrene derivative of formula (I) is selected from any one of formulae (1), (4), and (5).

Also, it is preferred according to the invention that $R^3$, $R^4$, $R^5$, and $R^6$ are the same or different and represent $CH_3$ or $C_6H_5$, and it is more preferred that $R^3$, $R^4$, $R^5$, and $R^6$ are the same and all represent $CH_3$. It is most preferred that $R^7$ and $R^8$ all represent $CH_3$, more preferably the styrene derivative is of Formula (1), (4), or (5) above.

Thus, the present invention in particular provides the following [bis(trimethylsilyl)amino]-functionalized styrenes:

1-[{N,N-bis(trimethylsilylamino)}(dimethylsilyl)]-2-{(4-vinylphenyl)dimethylsilyl}ethane with the formula (1),
1-[{N,N-bis(trimethylsilylamino)}(dimethylsilyl)]-2-{(4-vinylphenylmethyl)dimethylsilyl}ethane with the formula (4), and
1-[{N,N-bis(trimethylsilylamino)}(dimethylsilyl)]-2-{(3-vinylphenylmethyl)dimethylsilyl}ethane with the formula (5).

In a second aspect, the invention relates to a method for the preparation of a styrene derivative of Formula (I) above, wherein a silane of Formula (II)

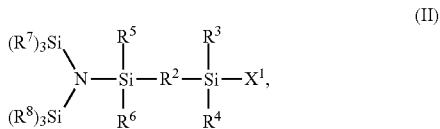

wherein $X^1$ is selected from chlorine, bromine, and iodine atoms, and $R^2$, $R^3$, $R^4$, $R^5$, $R^6$, $R^7$, and $R^8$ are as defined above, is reacted with a magnesium compound of Formula (III),

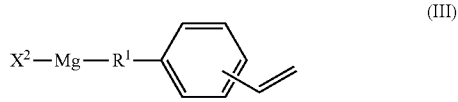

wherein $X^2$ is selected from chlorine, bromine, and iodine atoms, and $R^1$ is as defined above.

Preferably, the reaction is performed in an organic solvent in an inert gas atmosphere, more preferably the reaction is performed in an aliphatic or cyclic ether solvent (and in particular, the solvent is tetrahydrofuran, THF).

The organomagnesium compound with the formula (III) can be formed in situ either in the medium of the reaction between a halogenofunctional styrene with the general formula (IV),

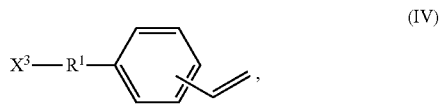

where $X^3$ is selected from chlorine, bromine, and iodine atoms) and magnesium in the presence of a silane with the formula (II), or can be introduced to the reaction medium (as a silane having the formula (II) as a ready-to-use reagent prepared in a separate reactor).

Due to the instability of the magnesium compound of formula (III), it is advantageous to conduct the reaction sequentially, i.e. to load the reactor with magnesium, the solvent (in any amount of e.g. about 10% of the required volume) and an activating agent (most advantageously iodine in the amount of e.g. about 0.005 mole per one mole of magnesium). During the activation of the magnesium surface with iodine, the reactor contents should be stirred and heated at solvent boiling point, until the brown color (of elemental iodine) disappears. Then, the silane with the formula (II) and subsequently the remaining part of the solvent are introduced to such a prepared system at room temperature. This is followed by the introduction of halogeno ($X^3$)-functional styrene with the general formula (IV), which is carried out in two steps, namely no more than 10 mol % of the amount of halogenofunctional styrene (resulting from the stoichiometric ratio) is initially introduced. After the reaction initiation (that is manifested by temperature increase), the remaining part of halogenofunctional styrene of formula (IV) is introduced step-by-step with such a rate that a gentle boiling of the solvent is maintained. The reaction proceeds at any ratio of reactants, however, in the case of using a reactant ratio different from the reaction stoichiometry many side products are formed. It is advantageous to conduct the reaction of the invention at 5 to 10 mole % excess of magnesium and at 3 to 6 mole % excess of halogenofunctional styrene with the general formula (III), each in relation to the silane of formula (II). The said reaction is preferably conducted at a temperature in the range of from 25° C. to 100° C., optimally at about 66° C. The reaction time is typically about 5 h.

The synthesis according to the second aspect of the invention is preferably carried out in a moisture-protected reactor, most advantageously in an argon or nitrogen atmosphere. The materials are introduced into the reactor sequentially, i.e. during the phase of magnesium surface activation the magnesium is introduced first, followed by the solvent and then by iodine, whereas during the reaction phase the sequence of the introduction (preferably at room temperature) is: silane (II) and then halogenofunctional styrene (IV). All liquid reagents, as well as the solvent, should preferably be dry and deoxygenated, to avoid the possibility of decomposition of silane (II) and organomagnesium compound (III) in the presence of any trace amounts of water and oxygen. Then the reaction mixture is heated and stirred until the reaction is completed.

The opposite sequence of introducing reagents to the activated magnesium-containing reactor, i.e. first the introduction of halogenofunctional styrene (with the general formula (IV)) and then silane (II) is also possible, but it can lead to a decrease in the desirable product yield as a result of partial polymerization of the compounds with the general formulas (III) and (IV).

The raw product of the reaction according to the second aspect of the invention is subjected to isolation by known methods. Generally, the isolation consists in evaporating the solvent from the post-reaction mixture followed by the separation of the product from magnesium halide $MgX^1X^2$ (that is formed as a side product of the reaction) and subjecting the obtained suspension to filtering or centrifuging. Separation is typically performed by extraction with an aliphatic hydrocarbon, advantageously with hexane or cyclohexane. The product is recovered from the filtrate by evaporating the solvent and volatile impurities under reduced pressure.

Compounds obtained according to the invention are applied as comonomeric substrates for obtaining styrene-butadiene rubbers with unique physicochemical properties. Thus, in a third aspect, the invention relates to the use of the styrene derivative of formula (I) in the preparation of a copolymer thereof.

Preferably, the copolymer comprises repeat units that are derived from
A) 20 wt. % to 99.95 wt. %, by weight of the copolymer, of one or more diene monomer(s);
B) 0 wt. % to 60 wt. %, by weight of the copolymer, of one or more vinyl aromatic monomer(s); and
C) 0.05 wt. % to 50 wt. %, by weight of the copolymer, of one or more styrene derivative(s) of formula (I)

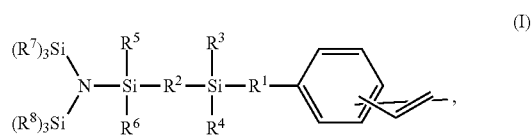

wherein $R^1$ and $R^2$ can be the same or different.

Further details of the use of the styrene derivative of the invention are disclosed in international application entitled "Elastomeric copolymers based on [bis(trihydrocarbylsilyl)aminosilyl]-functionalized styrene and their use in the preparation of rubbers", PCT/EP2016/057834, filed on even date herewith, the disclosure of which application is incorporated herein in its entirety. International application PCT/EP2016/057834 claims priority from EP15461525.6. EP15461525.6 was filed on even date with the present application's priority application, EP15461526.4.

The subject matter of the invention is presented in more detail in the examples, which illustrate, but do not limit, the invention.

The products were analyzed using:
$^1$H, and $^{13}$C NMR spectra, recorded with the use of NMR spectrometers of the types Bruker Ultra Shield 600 MHz and Bruker 500 MHz, and
GC-MS mass spectrometers of the types Bruker MS320 and GC-MS Varian Saturn 2000.

EXAMPLES

Example 1

A reactor of 1 L capacity, equipped with a magnetic stirrer, a dropping funnel and a reflux condenser equipped with a gas introduction attachment and an oil valve (Zaitsev washer), was loaded in argon atmosphere with magnesium metal (13.37 g, 0.55 mol), followed by addition of dry and deoxygenated tetrahydrofuran (THF, 200 mL) and iodine ($I_2$, 0.69 g, 2.75 mmol). This was followed by heating to 50° C., with stirring of the reactor contents. The activation of magnesium was conducted until disappearance of the brown color, followed by cooling of the reactor contents to room temperature. Then 1-[{N,N-bis(trimethylsilylamino)}(dimethylsilyl)]-2-{chlorodimethylsilyl}ethane (170.10 g, 0.50 mol) and the remaining part (300 mL) of the solvent were added to such a prepared activated magnesium. The dropping funnel was filled with 1-bromo-4-vinylbenzene (99 g, 0.53 mol). At the initiation step of the reaction, 9.90 mL of 1-bromo-4-vinylbenzene were added dropwise into the mixture without stirring the reactor contents. When clear symptoms of the reaction proceeding were observed, dosing of the remaining amount of halogenated vinylbenzene derivative began with such a rate that the reactor content boiled delicately for about 2 hours. After the dosing of 1-bromo-4-vinylbenzene was completed, the reactor temperature was maintained in the range of 60° C. for one hour, followed by cooling to room temperature. To neutralize a small excess of (4-vinylphenyl)magnesium bromide, 10 mL of 2-propanol were added. Then the solvent was evaporated from the post-reaction mixture under reduced pressure and 1.00 L of n-hexane was added to the residue. The obtained suspension was filtered off and the precipitate was washed with three portions of n-hexane of 200 mL each. Then the solvent was evaporated from the obtained filtrate under reduced pressure, followed by drying in a vacuum at 50° C. until a constant pressure was achieved. 191.70 g of 1-[{N,N-bis(trimethylsilylamino)}-(dimethylsilyl)]-2-{(4-vinylphenyl)dimethylsilyl}ethane were obtained with the yield of 94%. The product was subjected to spectroscopic analysis.

GC-MS: 408.4 (0.5); 407.4 (1.0); 381.4 (1.0); 380.4 (3.0); 379.3 (6.0); 220.3 (15.0); 219.3 (27.0); 218.3 (100); 217.6 (27.0); 216.2 (24.0); 204.2 (2.0); 203.2 (3.0); 202.1 (5.0); 188.1 (5.0); 161.1 (33.0); 145.1 (4.0); 131.1 (10.0); 130.0 (30.0); 100.0 (13.0); 73.1 (18.0); 59.1 (7.5).

NMR:

$^1$H NMR (300 MHz, CDCl$_3$, 300 K) δ(ppm)=7.49 (d, 2H, —C$_6$H$_4$—); 7.41 (d, 2H, —C$_6$H$_4$—); 6.73 (dd, 1H, —CH═); 5.79 (d, 1H, ═CH$_2$); 5.27 (d, 1H, ═CH$_2$); 0.66 (m, 2H, —CH$_2$—); 0.53 (m, 2H, —CH$_2$—); 0.28 (s, 6H, —SiMe$_2$-); 0.18 (s, 24H, —N(SiMe$_3$)$_2$, —SiMe$_2$-)

$^{13}$C NMR (75.46 MHz, CDCl$_3$, 300 K) δ(ppm)=139.23; 137.90; 136.92; 133.87; 125.48; 113.97; 12.58; 8.01; 5.55; 3.08; −3.55.

$^{29}$Si NMR (99.38 MHz, CDCl$_3$, 300 K) δ(ppm)=4.88; 2.29; −1.50

Example 2

A reactor of 20 L capacity, equipped with a magnetic stirrer, a dropping funnel and a reflux condenser equipped with a gas introduction attachment and an oil valve (Zaitsev washer), was loaded in argon atmosphere with magnesium metal (153.73 g, 6.32 mol), followed by addition of dry and deoxygenated tetrahydrofuran (THF, 1.00 L) and iodine (I$_2$, 7.97 g, 31.62 mmol). This was followed by heating to 50° C., with stirring of the reactor contents. The activation of magnesium was conducted until the disappearance of brown color, followed by cooling the reactor contents to room temperature. Then 1-[{N,N-bis(trimethylsilylamino)}(dimethylsilyl)]-2-{chlorodimethylsilyl}ethane (1956.20 g, 5.75 mol) and the remaining part (9.00 L) of the solvent were added to such a prepared activated magnesium. The dropping funnel was filled with 1-bromo-4-vinylbenzene (1,105 g, 6.04 mol). At the initiation step of the reaction, 100 mL of 1-bromo-4-vinylbenzene were added dropwise into the reaction system without stirring the reactor content. When clear symptoms of the reaction proceeding were observed, dosing of the remaining amount of halogenated styrene derivative began with such a rate that the reactor content boiled delicately for about 5 hours. After the dosing of 1-bromo-4-vinylbenzene was completed, the reactor temperature was maintained at about 60° C. for one hour, followed by cooling to room temperature. To neutralize a small excess of (4-vinylphenyl)magnesium bromide, 30 mL of 2-propanol were added. Then the solvent was evaporated from the post-reaction mixture under reduced pressure and 5.00 L of n-hexane was added to the residue. The obtained suspension was filtered off and the precipitate was washed with three 500 mL portions of n-hexane. Then the solvent was evaporated from the obtained filtrate under reduced pressure, followed by drying in a vacuum at 50° C. until a constant pressure was achieved. 2157.80 g of 1-[{N,N-bis(trimethylsilylamino)}(dimethylsilyl)]-2-{(4-vinylphenyl)dimethylsilyl}ethane were obtained with a yield of 92%.

Example 3

Acting in the same manner as in Example 1, 1-[{N,N-bis(trimethylsilylamino)}(dimethylsilyl)]-2-{chlorodimethylosilyl}ethane (78.82 g, 0.23 mol) was reacted with 1-(chloromethyl)-4-vinylbenzene (37.13 g, 0.24 mol) in the presence of 6.19 g (0.26 mol) of Mg activated with I$_2$ (0.38 g, 1.16 mmol). 91.03 g of 1-[{N,N-bis(trimethylsilylamino)}-(dimethylsilyl)]-2-{(4-vinylphenylmethyl)dimethylsilyl}ethane were obtained with the yield of 93%. The product was subjected to spectroscopic analysis.

GC-MS:

393.2 (0.9); 260.2 (3.4); 237.4 (2.0); 236.4 (10.3); 234.5 (41.4); 223.5 (2.6); 222.5 (12.7); 221.6 (19.1); 220.7 (100.0); 208.0 (2.8); 188.8 (1.4); 186.8 (1.5); 177.8 (1.7); 176.9 (2.3); 175.9 (14.8); 1517 (7.5); 117.7 (3.9); 100.5 (2.6); 73.3 (2.8).

NMR:

$^1$H NMR (300 MHz, CDCl$_3$, 300 K) δ(ppm)=7.28 (d, 2H, —C$_6$H$_4$—); 6.97 (d, 2H, —C$_6$H$_4$—); 6.67 (dd, 1H, —CH═); 5.68 (d, 1H, ═CH$_2$); 5.68 (d, 1H, ═CH$_2$); 5.16 (d, 1H, ═CH$_2$); 2.11 (s, 2H, —CH$_2$—); 0.51, 0.43 (m, 4H, —CH$_2$CH$_2$—); 0.21, 0.19, 0.18, −0.02 (s, 30H, —CH$_3$).

$^{13}$C NMR (75.46 MHz, CDCl$_3$, 300 K) δ(ppm)=140.43; 136.82; 133.34; 128.13; 126.08; 111.90; 25.12; 12.49; 7.15; 5.58; 3.06; −4.09.

$^{29}$Si NMR (99.38 MHz, CDCl$_3$, 300 K) δ(ppm)=4.85; 3.98; 2.31.

Example 4

Acting in the same manner as in Example 1, 1-[{N,N-bis(trimethylsilylamino)}(dimethylsilyl)]-2-{chlorodimethylosilyl}ethane (78.82 g; 0.232 mol) was reacted with a mixture of 1-(chloromethyl)-4-vinylbenzene and 1-(chloromethyl)-3-vinylbenzene (37.13 g; 0.24 mol) in the presence of 6.19 g (0.255 mol) of Mg activated with 0.38 g (1.16 mmol) of I$_2$. 88.10 g of a mixture of 1-[{N,N-bis(trimethylsilylamino)}(dimethylsilyl)]-2-{(4-vinylphenylmethyl)dimethylsilyl}ethane and 1-[{N,N-bis(trimethylsilylamino)}(dimethylsilyl)]-2-{(3-vinylphenylmethyl)dimethylsilyl}ethane were obtained with the yield of 90%.

GC-MS:

The para isomer: 393.2 (0.9); 260.2 (3.4); 237.4 (2.0); 236.4 (10.3); 234.5 (41.4); 223.5 (2.6); 222.5 (12.7); 221.6 (19.1); 220.7 (100.0); 208.0 (2.8); 188.8 (1.4); 186.8 (1.5); 177.8 (1.7); 176.9 (2.3); 175.9 (14.8); 151.7 (7.5); 117.7 (3.9); 100.5 (2.6); 73.3 (2.8).

The meta isomer: 237.3 (1.8); 236.3 (7.8); 235 (7.9); 234.4 (36.5); 223.5 (2.8); 222.5 (14.8); 221.5 (21.2); 220.6 (100.0); 219.0 (7.7); 207.9 (1.8); 186.7 (1.4); 188.7 (1.4); 177.7 (1.6); 176.8 (3.0); 175.8 (17.5); 151.6 (8.5); 149.7 (3.3); 100.4 (2.8); 73.2 (3.3).

NMR:

$^1$H NMR (300 MHz, CDCl$_2$, 300 K) δ(ppm)=7.28 (d); 7.17 (m); 7.06 (s); 6.98 (d); 6.92 (d) (—C$_6$H$_4$—); 6.69 (dd), 5.70 (dd); 5.19 (dd) (3H, —CH═CH$_2$); 2.11 (s, 2H, —CH$_2$—); 0.74 (m); 0.62 (m); 0.53 (m); 0.43 (m) (4H, —CH$_2$CH$_2$—); 0.22 (s); 0.21 (s), 0.20 (s) 0.18 (s); 0.17 (s); −0.01 (s); −0.02 (s) (30H, —CH$_3$).

$^{13}$C NMR (75.46 MHz, CDCl$_3$, 300 K) δ(ppm)=140.7; 140.43; 137.36; 137.21; 136.82; 133.35; 128.26; 128.13;

127.64; 126.08; 125.96; 121.83; 113.22; 111.90; 25.12; 12.49; 7.15; 7.12; 5.59; 3.10; −4.07; −4.06.

The invention claimed is:
1. A styrene derivative of formula (I)

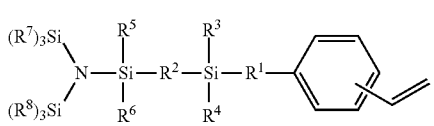
(I)

wherein $R^1$ and $R^2$ can be the same or different and represent a member selected from the group consisting of:
a) a single bond;
b) —$(CH_2)_n$—, wherein n represents an integer from 1 to 12;
c) —$(CH_2CH_2Y)_n$—, wherein n represents an integer from 1 to 12, and Y can independently be oxygen or sulfur;
d) —$CH_2$—$(CH_2CH_2Y)_n$—$CH_2$—, wherein n represents an integer from 1 to 12, and Y can independently be oxygen or sulfur;
e) —$(CH_2CH_2NR)_n$—, wherein n represents an integer from 1 to 12, and R can independently represent an alkyl group containing from 1 to 10 carbon atoms, or an aryl or aralkyl group containing from 6 to 10 carbon atoms;
f) —$CH_2$—$(CH_2CH_2NR)_n$—$CH_2$—, wherein n represents an integer from 1 to 12, and R can independently represent an alkyl group containing from 1 to 10 carbon atoms, or an aryl or aralkyl group containing from 6 to 10 carbon atoms;
g) —$(CH_2SiR_2)_n$—, wherein n represents an integer from 1 to 12, and R can independently represent an alkyl group containing from 1 to 10 carbon atoms, or an aryl or aralkyl group containing from 6 to 10 carbon atoms;
h) —$CH_2$—$(CH_2SiR_2)_n$—$CH_2$—, wherein n represents an integer from 1 to 12, and R can independently represent an alkyl group containing from 1 to 10 carbon atoms, or an aryl or aralkyl group containing from 6 to 10 carbon atoms;
i) —$(OSiR_2)_n$—, wherein n represents an integer from 1 to 12, and R can independently represent an alkyl group containing from 1 to 10 carbon atoms, or an aryl or aralkyl group containing from 6 to 10 carbon atoms; and
j) —$CH_2$—$(OSiR_2)_n$—$CH_2$—, wherein n represents an integer from 1 to 12, and R can independently represent an alkyl group containing from 1 to 10 carbon atoms, or an aryl or aralkyl group containing from 6 to 10 carbon atoms;
wherein $R^3$, $R^4$, $R^5$, and $R^6$ can be the same or different and represent an alkyl group containing from 1 to 10 carbon atoms, or an aryl or aralkyl group containing from 6 to 10 carbon atoms; and
$R^7$ and $R^8$ can be the same or different, and each $R^7$ and $R^8$ independently represents an alkyl group containing from 1 to 10 carbon atoms, or an aryl or aralkyl group containing from 6 to 10 carbon atoms.
2. The styrene derivative of claim 1, which is of Formula (Ia) or (Ib)

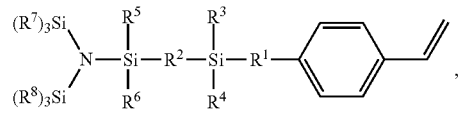
(Ia)

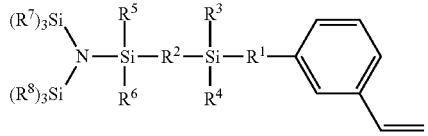
(Ib)

3. The styrene derivative of claim 1, wherein $R^1$ is selected from the group consisting of:
a) a single bond; and
b) —$(CH_2)_n$—, wherein n represents an integer from 1 to 12.
4. The styrene derivative of claim 3 wherein $R^1$ is —$(CH_2)_n$—, wherein n represents an integer from 1 to 5.
5. The styrene derivative of claim 3 wherein $R^1$ is —$(CH_2)_n$—, wherein n represents an integer from 1 to 3.
6. The styrene derivative of claim 3 wherein $R^1$ is —$(CH_2)_n$—, wherein n is 1.
7. The styrene derivative of claim 1 wherein $R^2$ is b) —$(CH_2)_n$—, wherein n represents an integer from 1 to 12.
8. The styrene derivative of claim 1 wherein $R^3$, $R^4$, $R^5$, and $R^6$ can be the same or different and represent $CH_3$ or $C_6H_5$.
9. The styrene derivative of claim 1 wherein $R^7$ and $R^8$ all represent $CH_3$.
10. A method of preparing a copolymer comprising copolymerizing a styrene derivative of claim 1.
11. The method of claim 10 wherein the copolymer comprises repeat units that are derived from
A) 20 wt. % to 99.95 wt. %, by weight of the copolymer, of one or more diene monomer(s);
B) 0 wt. % to 60 wt. %, by weight of the copolymer, of one or more vinyl aromatic monomer(s); and
C) 0.05 wt. % to 50 wt. %, by weight of the copolymer, of one or more styrene derivative(s) of formula (I)

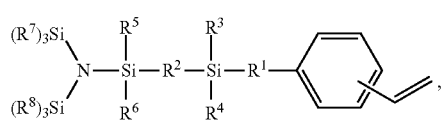
(I)

wherein $R^1$ and $R^2$ can be the same or different.
12. The styrene derivative of claim 1, wherein $R^1$ is selected from the group consisting of:
a) a single bond; and
b) —$(CH_2)_n$—, wherein n is 1 or 2.
13. The styrene derivative of claim 1, wherein $R^1$ is selected from the group consisting of:
a) a single bond; and
b) —$(CH_2)_n$—, wherein n is 1.
14. The styrene derivative of claim 1 wherein $R^2$ is b) —$(CH_2)_n$—, wherein n represents an integer from 1 to 5.
15. The styrene derivative of claim 1 wherein $R^2$ is b) —$(CH_2)_n$—, wherein n represents an integer from 1 to 3.
16. The styrene derivative of claim 1 wherein $R^2$ is b) —$(CH_2)_n$—, wherein n is 2.
17. The styrene derivative of claim 1 wherein $R^3$, $R^4$, $R^5$, and $R^6$ all represent $CH_3$.

18. The styrene derivative of claim 1 wherein the styrene derivative is of Formula (1), (2), (3), (4), (5), or (6):

(1)
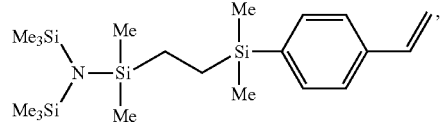

(2)
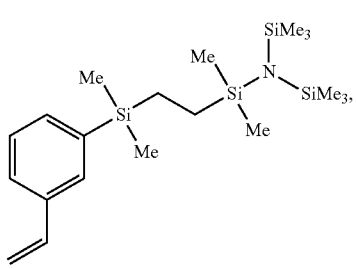

(3)
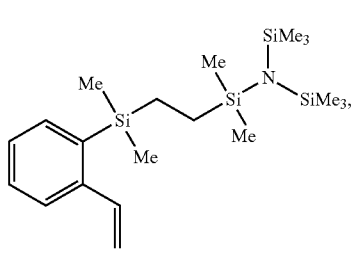

(4)
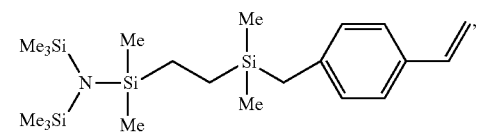

(5)
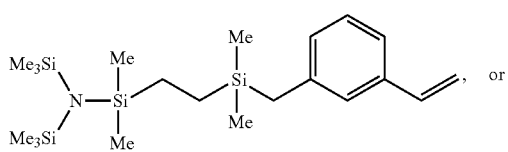

or (6)
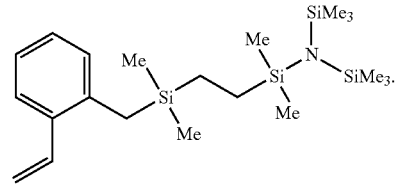

19. The styrene derivative of claim 1 wherein the styrene derivative is of Formula (1), (2), (4), or (5):

(1)
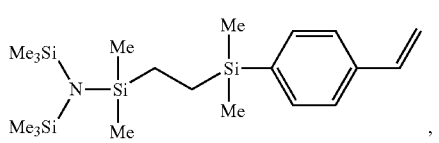

(2)
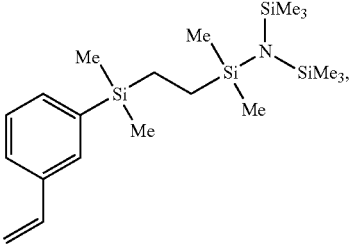

(4)
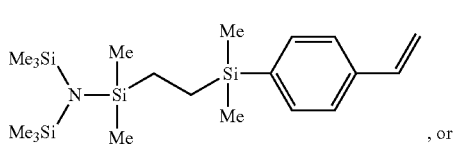

, or (5)
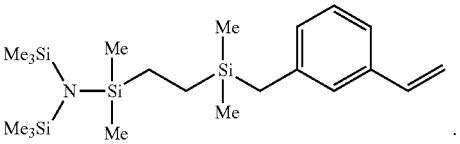

20. The styrene derivative of claim 1 wherein the styrene derivative is of Formula (1), (4), or (5):

(1)
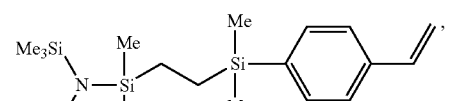

(4)
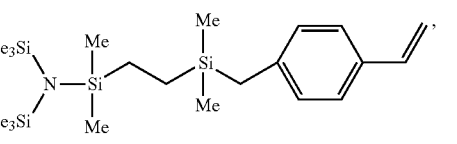

or (5)
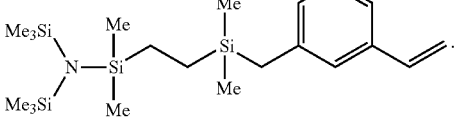

21. A method for the preparation of a styrene derivative of Formula I (I)
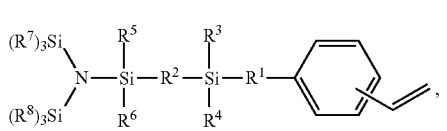

wherein $R^1$ and $R^2$ can be the same or different and represent a member selected from the group consisting of:
a) a single bond;
b) —$(CH_2)_n$—, wherein n represents an integer from 1 to 12;
c) —$(CH_2CH_2Y)_n$—, wherein n represents an integer from 1 to 12, and Y can independently be oxygen or sulfur;

d) —CH$_2$—(CH$_2$CH$_2$Y)$_n$—CH$_2$—, wherein n represents an integer from 1 to 12, and Y can independently be oxygen or sulfur;

e) —(CH$_2$CH$_2$NR)$_n$—, wherein n represents an integer from 1 to 12, and R can independently represent an alkyl group containing from 1 to 10 carbon atoms, or an aryl or aralkyl group containing from 6 to 10 carbon atoms;

f) —CH$_2$—(CH$_2$CH$_2$NR)$_n$—CH$_2$—, wherein n represents an integer from 1 to 12, and R can independently represent an alkyl group containing from 1 to 10 carbon atoms, or an aryl or aralkyl group containing from 6 to 10 carbon atoms;

g) —(CH$_2$SiR$_2$)$_n$—, wherein n represents an integer from 1 to 12, and R can independently represent an alkyl group containing from 1 to 10 carbon atoms, or an aryl or aralkyl group containing from 6 to 10 carbon atoms;

h) —CH$_2$—(CH$_2$SiR$_2$)$_n$—CH$_2$—, wherein n represents an integer from 1 to 12, and R can independently represent an alkyl group containing from 1 to 10 carbon atoms, or an aryl or aralkyl group containing from 6 to 10 carbon atoms;

i) —(OSiR$_2$)$_n$—, wherein n represents an integer from 1 to 12, and R can independently represent an alkyl group containing from 1 to 10 carbon atoms, or an aryl or aralkyl group containing from 6 to 10 carbon atoms; and j) —CH$_2$—(OSiR$_2$)$_n$—CH$_2$—, wherein n represents an integer from 1 to 12, and R can independently represent an alkyl group containing from 1 to 10 carbon atoms, or an aryl or aralkyl group containing from 6 to 10 carbon atoms;

wherein R$^3$, R$^4$, R$^5$, and R$^6$ can be the same or different and represent an alkyl group containing from 1 to 10 carbon atoms, or an aryl or aralkyl group containing from 6 to 10 carbon atoms; and R$^7$ and R$^8$ can be the same or different, and each R$^7$ and R$^8$ independently represents an alkyl group containing from 1 to 10 carbon atoms, or an aryl or aralkyl group containing from 6 to 10 carbon atoms;

wherein a silane of Formula (II)

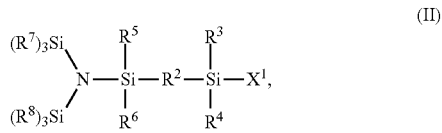

wherein X$^1$ is selected from chlorine, bromine, and iodine atoms, and R$^2$, R$^3$, R$^4$, R$^5$, R$^6$, R$^7$, and R$^8$ are as defined above is reacted with a magnesium compound of Formula (III),

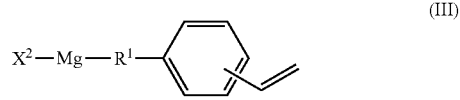

wherein X$^2$ is selected from chlorine, bromine, and iodine atoms, and R$^1$ is as defined above.

22. The method of claim 21, wherein the reaction is performed in an organic solvent in an inert gas atmosphere.

23. The method of claim 21, wherein the reaction is performed in an organic solvent in an inert gas atmosphere, wherein the organic solvent comprises an aliphatic or cyclic ether solvent.

24. The method of claim 21, wherein the reaction is performed in an organic solvent in an inert gas atmosphere, wherein the organic solvent comprises tetrahydrofuran (THF).

* * * * *

UNITED STATES PATENT AND TRADEMARK OFFICE
CERTIFICATE OF CORRECTION

PATENT NO.       : 10,259,830 B2
APPLICATION NO.  : 15/565338
DATED            : April 16, 2019
INVENTOR(S)      : Maciejewski et al.

Page 1 of 1

It is certified that error appears in the above-identified patent and that said Letters Patent is hereby corrected as shown below:

In the Claims

Column 13, Line 61, Claim (19) should read:
--- 19. The styrene derivative of claim 1 wherein the styrene derivative is of Formula (1), (2), (4), or (5):

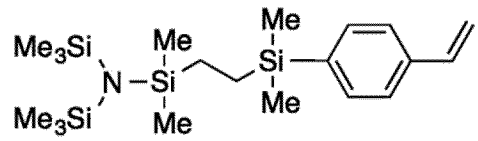

(1)       ,

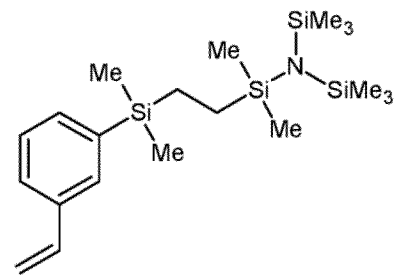

(2),

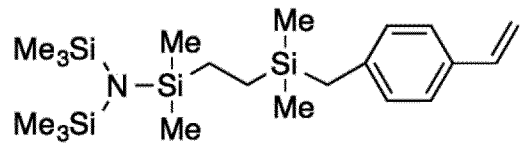

(4)       , or

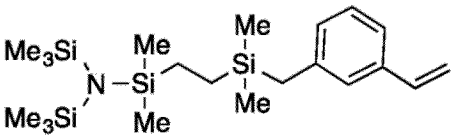

(5).       ---

Signed and Sealed this
First Day of October, 2019

Andrei Iancu
*Director of the United States Patent and Trademark Office*